United States Patent [19]

Waterbury

[11] Patent Number: 4,558,066
[45] Date of Patent: Dec. 10, 1985

[54] TREATMENT AND PREVENTION OF OCULAR HYPERTENSION

[75] Inventor: L. David Waterbury, San Mateo, Calif.

[73] Assignee: Syntex (U.S.A.) Inc., Palo Alto, Calif.

[21] Appl. No.: 611,245

[22] Filed: May 17, 1984

[51] Int. Cl.$^4$ .............................................. A61K 31/40
[52] U.S. Cl. ................................................... 514/422
[58] Field of Search ........................................ 424/274

[56] References Cited

U.S. PATENT DOCUMENTS

| | | | |
|---|---|---|---|
| 3,655,693 | 4/1972 | Shen et al. | 260/332.2 A |
| 3,987,200 | 10/1976 | Tuttle et al. | 424/330 |
| 4,275,074 | 6/1981 | Langham | 424/280 |
| 4,312,863 | 1/1982 | Gold et al. | 424/230 |
| 4,322,425 | 3/1982 | Yabuuchi et al. | 424/258 |
| 4,342,692 | 8/1982 | Suh et al. | 424/274 |

Primary Examiner—Douglas W. Robinson
Attorney, Agent, or Firm—Ellen J. Buckles; Tom M. Moran; Alan M. Krubiner

[57] ABSTRACT

This invention relates to a method of treatment of ocular hypertension and to a topical ophthalmic pharmaceutical composition useful for management of ocular hypertension.

When administered topically to an eye with increased intraocular pressure, ±2-[(3,4-methylenedioxy)phenethyl]-5-[(3-carboxamido-4-hydroxy)-α-hydroxybenzyl]-pyrrolidines effectively decrease intraocular pressure, inhibit the deterioration of the eye due to intraocular hypertension or glaucoma and relieve the symptoms of already existing glaucoma or other ophthalmic disease.

11 Claims, No Drawings

TREATMENT AND PREVENTION OF OCULAR HYPERTENSION

BACKGROUND OF THE INVENTION

1. Field of the Invention

This invention is directed to a novel method for relieving, inhibiting or preventing ophthalmic diseases caused by or associated with increased intraocular pressure. The method is particularly useful in the number of clinical cases included in the category of glaucoma.

Compound ±2-[(3,4-methylenedioxy)phenethyl]-5-[(3-carboxamido-4-hydroxy)-α-hydroxybenzyl]pyrrolidine, any of its stereoisomers and their pharmaceutically acceptable acid addition salts have been shown to lower intraocular pressure in mammals and are, therefore, useful in the treatment of all ophthalmic diseases which profess the increased intraocular pressure. Although these compounds are particularly useful in treatment of glaucoma, the other ophthalmic diseases which are accompanied with or caused by increased intraocular pressure will also respond to the treatment.

Compounds of this invention profess several advantages over existing treatment of intraocular pressure. They are non-irritating to the eye, they have long lasting activity, they do not show contralateral effect, they lack systemic activity, and they are as, or more, effective than labetolol or timolol, a known intraocular pressure lowering agent.

2. Related Disclosures

Attempts to find effective treatment of ocular hypertension are known. Catecholamine treatment of ocular hypertension is described in U.S. Pat. No. 4,275,074. Treating glaucoma and lowering intraocular pressure by topical administration of R,R-labetolol is described in U.S. Pat. No. 4,312,863. Reducing intraocular pressure in glaucomatous dogs with N-demethylated carbachol is described in *Invest. Ophthalmic Vis. Sci.*, 19:1198 (1980). U.S. Pat. No. 4,322,425 describes an ophthalmic composition containing a carbostyril derivative useful for treatment of glaucoma.

The compounds of this invention are the subject of the currently pending patent applications Ser. No. 460,204 and Ser. No. 527,716 describing their systemic hypotensive effect. These compounds were not previously administered topically, i.e., directly to the eye, to prevent, inhibit or treat ophthalmic diseases because their non-irritating properties to the eye were unknown, and are unexpected and surprising.

SUMMARY OF THE INVENTION

One aspect of this invention concerns a novel method for the treatment of certain ophthalmic diseases in mammals, particularly those diseases associated with or caused by increased intraocular pressure such as for example, glaucoma.

The method comprises administering directly to the eye of a mammal in need of such treatment a pharmaceutically effective amount of compound of the formula

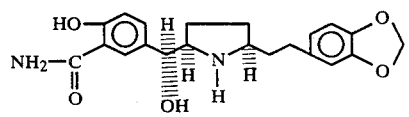

or any of its stereoisomers or their pharmaceutically acceptable acid addition salt.

Another aspect of this invention relates to the method for treatment of elevated intraocular pressure with the mixture of, or with individual stereoisomers, namely cis erythro, cis threo, trans erythro and trans threo isomers of the above compound.

Yet another aspect relates to the ophthalmologically acceptable topical pharmaceutical composition useful for treatment and prevention of elevated intraocular pressure and glaucoma.

DETAILED DESCRIPTION OF THE INVENTION

Definitions

As used hereinafter:

"Ophthalmic diseases" as used hereinafter mean ocular disorders which are either caused by, or associated with, increased intraocular pressure and include, but are not limited to, all forms of glaucoma as defined in *The Merck Manual* cited above.

"Mammals" means a class of warm-blooded vertebrates characterized by mammary glands, including but not limited to humans, laboratory or domestic animals such as dogs, cats, mice, rats or rabbits, and livestock.

"Treatment" covers any treatment of the disease in a mammal, particularly human, and includes (i) preventing the disease from occuring in a subject which may be predisposed to the disease but has not yet been diagnosed as having it, (ii) inhibiting the disease, i.e. arresting the development of said disease, or (iii) relieving the symptoms of the disease, i.e. causing regression of the disease.

"Noble metal catalyst" is a catalyst such as platinum on carbon, platinum oxide, palladium on carbon, or rhodium on carbon, but other noble metal catalysts suitable to effect catalytic reductions are also included.

"Protection" or "Protecting group" refer to the protection of phenolic hydroxyl groups. A phenolic hydroxyl group is present in compounds prepared by the process of this invention. In order to preserve the phenolic hydroxyl group during the catalytic reduction, O-protection is often required for phenols, which react readily with oxidizing agents, electrophiles, or even with mild alkylating and acylating agents. The protection of phenolic hydroxyl groups can be achieved with any suitable protecting group such as an alkyl ether, for example methyl ether, isopropyl ether, t-butyl ether; alkoxymethyl ether, for example methoxymethyl ether; alkoxyethoxymethyl ether, for example methoxyethoxymethyl ether; cycloalkylmethyl ether, for example cyclopropylmethyl ether; alkyldimethylsilyl ether, for example t-butyldimethylsilyl ether, 9-anthrylmethyl ether, preferably substituted or unsubstituted benzyl ether. [*Protective Groups in Organic Synthesis*, John Wiley & Sons, New York, pp: 87–100(1980); Synthesis, (II): 987 (1982)].

"N-Protection" or "N-Protecting groups" refer to electron withdrawing groups which make pyrrole less aromatic and more susceptible to the reduction. Electron withdrawal achieved through the utilization of N-protection of the nitrogen atom of the pyrrole can be best illustrated by attachment of the acyl N-protecting group, i.e.

where R may be aryl, phenyl, substituted phenyl, alkyl of 1-4 carbons with branched alkyl preferred, alkoxy of 1-4 carbons with branched alkoxy preferred. Exemplary N-protecting groups for the pyrrole nitrogen atom are alkoxycarbonyl such as methoxycarbonyl, ethoxycarbonyl, propoxycarbonyl, t-butoxycarbonyl and the like, or alkylcarbonyl such as methylcarbonyl, ethylcarbonyl, propylcarbonyl and the like, or alkanoyl such as ethanoyl, propanoyl, butanoyl and the like, or aroyl.

"Aroyl" means the radical ZCO— wherein Z is an aromatic group such as, for example, benzoyl or naphthoyl.

"Wt %" (weight percent) used for solids means the weight of one solid relative to the total weight of all reactants. For example, if 10 wt % of catalyst is given, then 10 g of catalyst are added for 90 g of other reactants.

"Mild reaction conditions" means that the reaction is run at the low temperatures between 10°–35° C., preferably ambient and at pressures of 1–5 atmospheres, preferably at atmospheric pressure, in the presence of a suitable organic solvent.

"Organic solvent" means liquid organic compound with the power to dissolve solids or liquids at mild reaction conditions. The term is meant to include cyclic and acyclic compounds such as alcohols of 1–4 carbons, lower alkyl esters or alkanoic acids, ethers, cyclic ethers and the like. Examplary solvents are methanol, ethanol, ethyl acetate, tetrahydrofuran, benzene or mixtures thereof.

"Lower alkyl" means a branched or unbranched saturated hydrocarbon chain containing from one to four carbon atoms, such as, for example, methyl, ethyl, n-propyl, iso-propyl, n-butyl, iso-butyl and the like.

"Cycloalkyl" means a saturated monocyclic hydrocarbon of 3–7 carbons without side chains, such as cyclopropane, cyclobutane, cyclopentane, cyclohexane and cycloheptane.

"Alkoxy" means —OR wherein R is lower alkyl as defined hereinabove.

"Alkoxycarbonyl" means —C(O)—OR wherein R is lower alkyl as defined hereinabove.

"Alkylcarbonyl" means —C(O)—R wherein R is lower alkyl as defined hereinabove.

Hereinafter "α-hydroxybenzyl" or "phenylhydroxymethyl" mean compounds of the formula

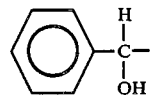

"Strong acid" means an organic or inorganic, water soluble, easily dissociable Bronsted Lowry acid, such as methanesulfonic, trifluoroacetic, hydrochloric, sulfuric, phosphoric acid and the like.

"Strong base" means an inorganic, water soluble base such as sodium hydroxide, sodium carbonate, potassium carbonate, and the like.

"N-acylating" means the formation or introduction of acyl radical

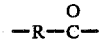

to the N-atom of the pyrrole ring.

"Ph" in reaction schemes drawings means phenol.

"Lower alkyl" means a branched or unbranched saturated hydrocarbon chain of 1–6 carbons, such as, for example, methyl, ethyl, n-propyl, i-butyl and the like.

"Optionally substituted lower phenylalkyl" means a moiety in which the phenyl, which may or may not be substituted as described above, is attached to the compounds of this invention by an intervening lower alkyl. Such embodiments of "optionally substituted phenyl lower alkyl", are, for example benzyl, phenylethyl, 2-(4-fluorophenyl)ethyl 3-(3,5-dimethylphenyl)-n-propyl and the like.

"Substituted phenyl" means a phenyl group which has one or two substituents selected from the group of hydroxy, lower alkyl, lower alcoxy or halo groups. Typical substituted phenyl groups include, for example, p-hydroxyphenyl, p-ethylphenyl, p-t-butoxyphenyl and the like.

"Alkenyl" means monoethylenically unsaturated linear or branched acyclic hydrocarbon chain such as propenyl, butenyl, pentenyl, phexenyl and the like.

"Lower alkenyl" means an unsaturated linear or branched alkenyl as defined above with a chain of 1–6 carbons, such as, for example, vinyl (ethenyl), propenyl, butenyl and such.

"Carbocycle" means a homocyclic ring compound in which all the ring atoms are carbon. Typical carbocycles are benzene, bicyclohexyl, tricyclodecyl and such.

Pharmaceutically acceptable salts refers to pharmaceutically acceptable hydrogen-anion addition salts which do not adversely affect the pharmaceutical properties of the parent compounds. With respect to the addition salts, suitable inorganic anions include, for example, chloride, bromide, iodide, sulfate, phosphate, nitrate, sulfate and the like. Suitable organic anions include, for example, acetate, benzoate, lactate, picrate, propionate, butyrate, valerate, tartrate, maleate, fumarate, citrate, succinate, tasylate, ascorbate, nicotinate, adipate, gluconate and the like.

Stereochemical Control

The ±2-[(3,4-methylenedioxy)phenethyl]-5-[(3-carboxamido-4-hydroxy)-α-hydroxybenzyl]pyrrolidines have three chiral centers. Two chiral centers are at the 2- and 5-positions of the pyrrolidine ring at which the side chains are substituted. The third chiral center is introduced in pyrrolidines where the side chain attached to the 5-position is α-hydroxybenzyl.

Compounds with three chiral centers can be obtained as four diastereoisomeric racemates or as eight optical isomers in total. The nomenclature (±)cis erythro, (±)cis threo, (±)trans erythro and (±)trans threo is used to describe individual diastereoisomers.

Embodiments wherein hydrogens at 2- and 5-positions are on the same side of the plane of the pyrrolidine ring are designated "cis". Embodiments where hydrogens at 2- and 5-position are on opposite sides are "trans."

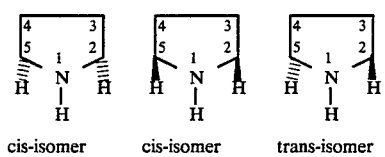

cis-isomer    cis-isomer    trans-isomer

"Erythro/threo" terminology is used to designate the relationship between the configurations of the group attached to the carbon atom bearing the hydroxyl substituent and of the number 5 carbon of the pyrrolidine ring to which it is attached.

"Erythro" indicates those embodiments wherein the hydrogen of carbon atom 5 of the ring and the hydrogen of the hydroxylated carbon occupy the same side of the molecule.

"Threo" indicates those embodiments where the hydrogen of carbon atom 5 of the ring and the hydrogen of the hydroxylated carbon are on the opposite sides of the molecule. For the numbering system, see below.

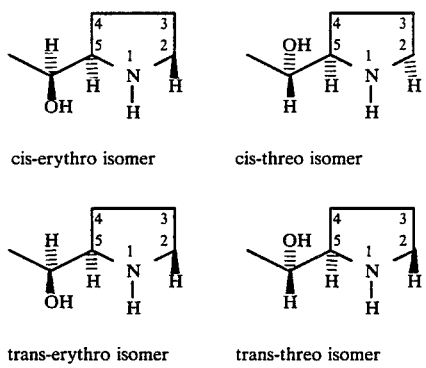

cis-erythro isomer    cis-threo isomer trans-erythro isomer    trans-threo isomer See *Stereochemistry of Carbon Compounds*, McGraw-Hill, pp. 16–86 (1962); *RECUEIL*, 83:535, (1964); and Morison and Boyd, *Organic Chemistry*, 3d Ed., pp. 148–153, (1974).

Numbering on the phenyl rings of the pyrrole or pyrrolidine molecule is illustrated below.

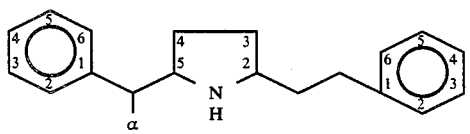

It is to be understood that this invention discloses and encompasses each of the racemates, racemic mixtures, diastereomers and enantiomers.

PREFERRED EMBODIMENTS

One preferred embodiment useful in the method of the current invention is the compound of the formula

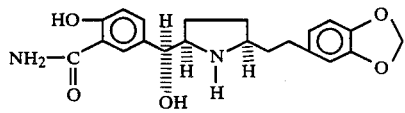

namely, ±2-[(3,4-methylenedioxy)phenethyl]-5-[(3-carboxamido-4-hydroxy)-α-hydroxybenzyl]pyrrolidine or its pharmaceutically acceptable non-toxic salt.

Another preferred embodiment useful in the method of the current invention is the compound of the formula

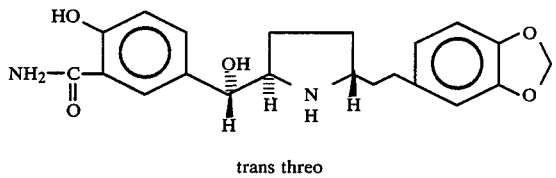

trans threo namely, ±trans threo 2-[(3,4-methylenedioxy)phenethyl]-5-[(3-carboxamido-4-hydroxy)-α-hydroxybenzyl]-pyrrolidine or its pharmaceutically acceptable non-toxic salt.

More preferred embodiment useful in the method of the current invention is the compound of the formula

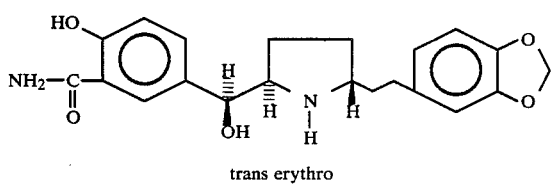

trans erythro namely, ±trans erythro 2-[(3,4-methylenedioxy)phenethyl]-5-[(3-carboxamido-4-hydroxy)-α-hydroxybenzyl]-pyrrolidine, or its pharmaceutically acceptable non-toxic salt.

Even more preferred embodiment useful in the method of the current invention is the compound of the formula

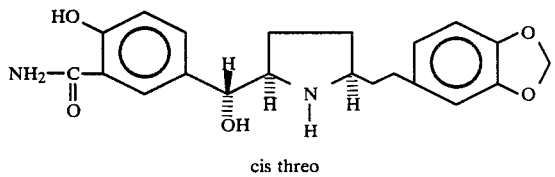

cis threo namely, ±cis threo 2-[(3,4-methylenedioxy)phenethyl]-5-[(3-carboxamido-4-hydroxy)-α-hydroxybenzyl]pyrrolidine, or its pharmaceutically acceptable non-toxic salt.

Most preferred embodiment useful in the method of the current invention is the compound of the formula

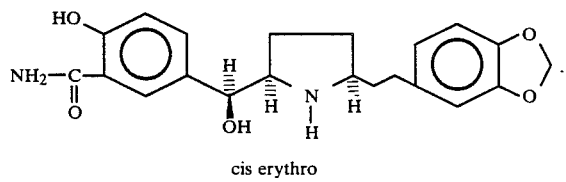

cis erythro namely, ±cis erythro 2-[(3,4-methylenedioxy)phenethyl]-5-[(3-carboxamido-4-hydroxy)-α-hydroxybenzyl]-pyrrolidine or its pharmaceutically acceptable salt.

PREPARATION PROCEDURES

A compounds of this invention are prepared by the reaction sequence illustrated in Reaction Schemes 1–4.

Reaction Scheme 1 illustrates the preparation of ±cis erythro 2-[(3,4-methylenedioxy)phenethyl]-5-[(3-carboxamido-4-hydroxy)-α-hydroxybenzyl]pyrrolidine.

Reaction Scheme 2 illustrates the preparation of ±cis threo 2-[(3,4-methylenedioxy)phenethyl]-5-[(3-carboxamido-4-hydroxy)-α-hydroxybenzyl]pyrrolidine.

Reaction Scheme 3 illustrates preparation of ±trans erythro 2-[(3,4-methylenedioxy)phenethyl]-5-[(3-carboxamido-4-hydroxy)-α-hydroxybenzyl]pyrrolidine.

Reaction Scheme 4 illustrates preparation of ±trans threo 2-[(3,4-methylenedioxy)phenethyl]-5-[(3-carboxamido-4-hydroxy)-α-hydroxybenzyl]pyrrolidine.

REACTION SCHEME 1

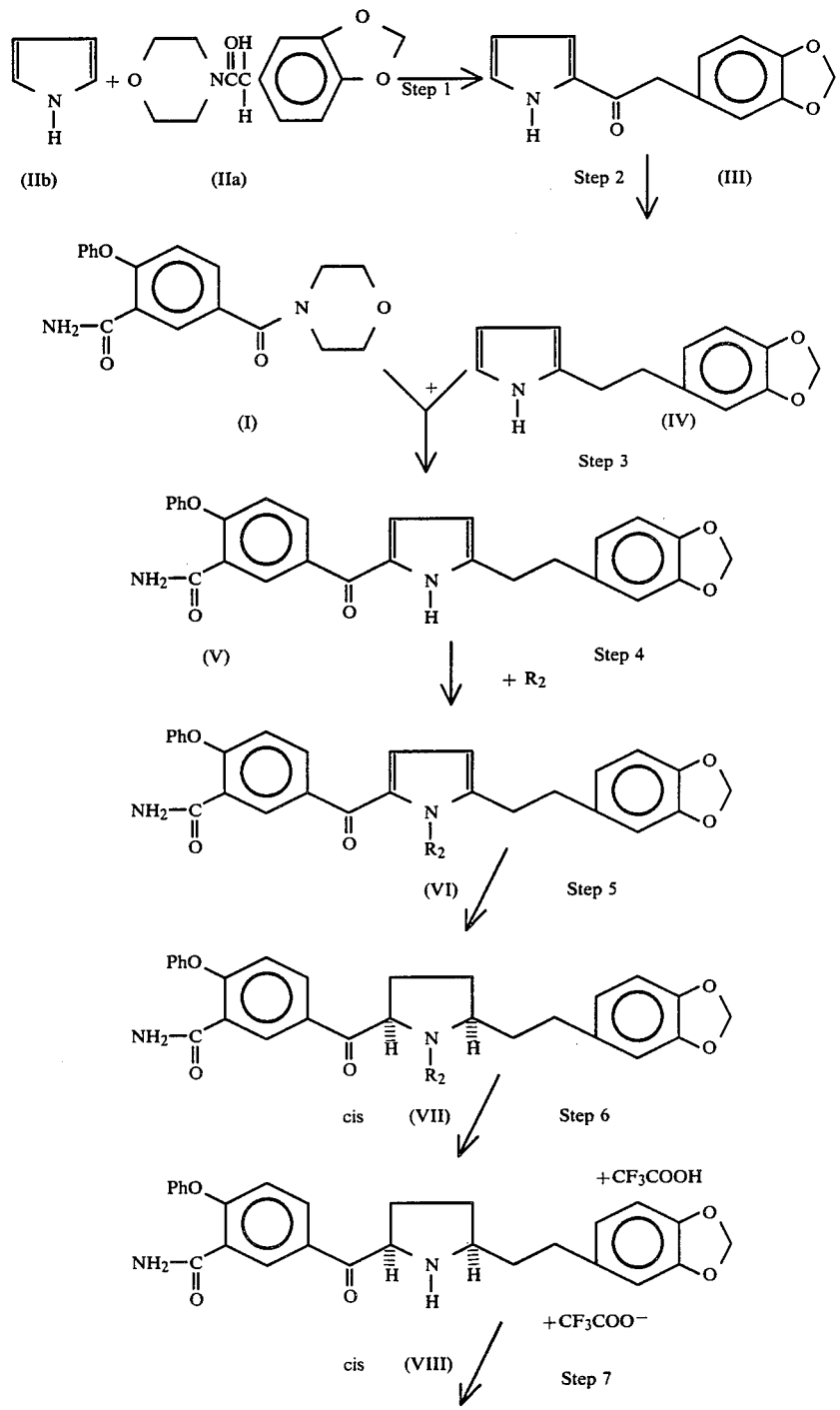

-continued
REACTION SCHEME 1

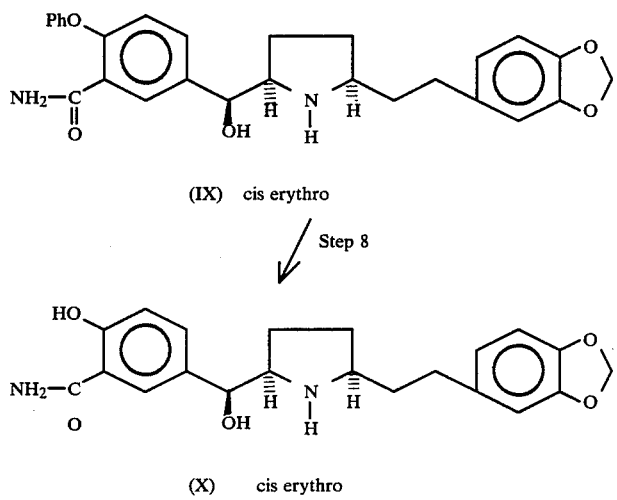

(IX) cis erythro

Step 8

(X) cis erythro

Step 1. Step 1 describes the preparation of 2-[(3,4-methylenedioxy)phenylacetyl]pyrrole (III) from pyrrole (IIb) and [(3,4-methylenedioxy)phenylacetyl]morpholide (IIa).

Pyrrole (IIb) is commercially available from Aldrich. [(3,4-methylenedioxy)phenylacetyl]morpholide (IIa) is prepared by reacting phenylacetic acid with thionyl chloride and with a small amount of dimethylformamide for 10–60 minutes at the temperature of 10°–30° C., preferably at room temperature. The resulting mixture is reacted with morpholine dissolved in an organic solvent, preferably in dry dichloromethane, to give [(3,4-methylenedioxy)phenylacetyl]morpholide (IIa).

[(3,4-methylenedioxy)phenylacetyl]morpholide (IIa) in the presence of an acylating agent, such as acid halides, preferably phosphorous oxychloride, is reacted under the constant stirring for 3–10 hours, preferably for 6 hours. Pyrrole (IIb) dissolved in a chlorinated hydrocarbon solvent, preferably in anhydrous 1,2-dichloroethane, is added. The reaction mixture is stirred for 12–20 hours, alkalized, and purified by methods known in the art to obtain 2-[(3,4-methylenedioxy)phenylacetyl]pyrrole (III).

Step 2. Step 2 describes the conversion of 2-[(3,4-methylenedioxy)phenylacetyl]pyrrole (III) to 2-[(3,4-methylenedioxy)phenethyl]pyrrole (IV).

Compound (III) is dissolved in an ethereal solvent, preferably dry tetrahydrofuran, and a complex metal hydride, preferably lithium aluminum hydride, is added. The mixture is reacted at reflux temperature for 35–55 hours, preferably 48 hours. Excess of hydride is destroyed with an organic solvent and the reaction mixture is purified by methods known in the art to afford 2-[(3,4-methylenedioxy)phenethyl]pyrrole (IV).

Step 3. Step 3 describes the preparation of 2-[(3,4-methylenedioxy)phenethyl]-5-[(3-carboxyamido-4-benzyloxy)benzoyl]pyrrole (V).

[(3-carboxamido-4-benzyloxy)benzoyl]morpholide (I) is prepared from (3-carboxamido-4-benzyloxy)benzoic acid by procedure similar to that of Step 1. (3-carboxamido-4-benzyloxy)benzoic acid, in turn, is prepared from (3-carboxamido-4-hydroxy)benzoic acid which is a known compound of which preparation is described in Brit. Pat. No. 802,841, issued Oct. 15, 1958, in J. Chem. Soc., pp. 4678 (1956), and in Chem. in Industry, pp. 417 (1955)).

It should be noted that in order to prepare ±cis erythro 2-[(3,4-methylenedioxy)phenethyl]-5-[(3-carboxamido-4-hydroxy)benzoyl]pyrrole (X), 4-hydroxy phenolic group of the compounds undergoing reaction steps 3–7, 9–10, 12–14 and 16–17 must be protected. Usually, such protection is achieved with benzylation of phenolic hydroxy group. Therefore, compound I with benzyloxy protecting group must be prepared.

Benzylation of phenolic hydroxy group begins with dissolving methyl ester of (3-carboxamido-4-hydroxy)-benzoic acid in an organic solvent, preferably in dimethylformamide, and treating it with metal hydride, preferably with 1 equivalent of sodium hydride, at a temperature of 10°–30° C., preferably at room temperature. The mixture is stirred until the compounds dissolve, for about 5–6 minutes and benzyl halide, preferably benzyl bromide or chloride is added. The mixture is again stirred at a temperature of 15°–50° until reaction is complete, usually for 1–3 hours. The mixture is purified with methods known in the art and the methyl ester (3-carboxamido-4-benzyloxy)benzoic acid is hydrolyzed with aqueous bicarbonate or carbonate in lower alcohol such as methanol or ethanol to obtain (3-carboxamido-4-benzyloxy)benzoic acid which is then submitted to the same procedure as described in Step 1 to obtain [(3-carboxamido-4-benzyloxy)benzoyl]morpholide (I).

Alternately, the compound (X) may also be prepared from the (3-nitrile-4-hydroxy)benzoic acid. This compound is known and is described in German Pat. No. 2,224,681, issued on Oct. 10, 1970, and in corresponding Brit. Applic. No. 16197-7), published on May 21, 1971.

(3-nitrile-4-hydroxy)benzoic acid is benzylated using the procedure described above for (3-carboxamido-4-hydroxy)benzoic acid and as such, i.e. (3-nitrile-4-benzyloxy)benzoic acid, (3-nitrile-4-benzyloxy)benzoyl and (3-nitrile-4-benzyloxy)α-hydroxybenzyl is carried through the Steps 3–7, 9–10, 12–14 and 16–17. Before debenzylating Steps 8, 11, 15 and 18, a nitrile compound is hydrolyzed to the carboxamido with 10–20% aqueous hydrochloric acid in a polar solvent such as, for example, methanol for about 0.5–5 hours. The nitrile compound can also be hydrolyzed to its corresponding carboxamido compound with 1 equivalent of aqueous sodium hydroxide in a polar solvent.

[(3-carboxamido-4-benzyloxy)benzoyl]morpholide is reacted with an acylating agent, preferably phosphorous oxychloride, at a room temperature for 2-4 hours. Then the compound (IV), dissolved in an organic solvent, preferably in 1,2-dichloroethane, is added and the mixture is stirred for 15-21 hours, preferably for 18 hours. The mixture is purified by methods known in the art to give ±2-[(3,4-methylenedioxy)phenethyl]-5-[(3-carboxamido-4-benzyloxy)benzoyl]pyrrole (V).

Step 4. Step 4 describes the attachment of the protective group $R_2$ to the N atom of the pyrrole compound (V).

Compound (V) is dissolved in a suspension of an ethereal or dipolar solvent, preferably in dry dimethylformamide, and mixed with sodium hydride. The mixture is heated to 45°-60° for 1-3 hours, preferably 2 hours. Suitable N-protecting agent $R_2$, such as aroylchloride, alkanoylchloride, alkylchloroformate, preferably di-t-butylcarbonate, is added and the mixture is stirred at 60°-70° for 1-3 hours. After purification and crystallization by methods known in the art, ±N-protected-2-[(3,4-methylenedioxy)phenethyl]-5-[3-carboxamido-4-benzyloxy)benzoyl]pyrrole, preferably ±1-t-butoxycarbonyl-2-[(3,4-methylenedioxy)phenethyl]-5-[(3-carboxamido-4-benzyloxy)benzoyl]pyrrole (VI) is obtained.

Step 5. Step 5 describes a catalytic reduction of ±1-t-butoxycarbonyl-2-[(3,4-methylenedioxy)phenethyl]-5-[(3-carboxamido-4-benzyloxy)benzoyl]pyrrolidine (VII).

Pyrrole (VI) is reduced in the presence of the noble metal catalyst, such as rhodium on carbon, rhodium on aluminum, platinum oxide, preferably with platinum on carbon, in the solvent or solvent mixture containing lower alcohol, lower alkyl ester or ethereal solvent. The preferred solvent is ethyl acetate. Reduction is carried on under the mild reaction conditions, at the room temperature and pressure of 1-3 atmospheres, preferably at atmosphere pressure for 15-28 hours, preferably for 22 hours. The reduced compound is purified and crystallized by the methods known in the art to give ±cis 1-t-butoxycarbonyl-2-[(3,4-methylenedioxy)-phenethyl]-5-[(3-carboxamido-4-benzyloxy)benzoyl]-pyrrolidine (VII).

Step 6. Step 6 describes the removal of the N-protecting $R_2$ group from the compound (VII).

A solution of ±cis 1-t-butoxycarbonyl-2-[(3,4-methylenedioxy)phenethyl]-5-[(3-carboxamido-4-benzyloxy)benzoyl]pyrrolidine (VII) in chlorinated hydrocarbon, preferably dry dichloromethane, is added to a strong protic acid, preferably trifluoroacetic acid. The reaction is carried on for 1-3 hours at room temperature. After purification and crystallization by methods known in the art, ±cis 2-[(3,4-methylenedioxy)phenethyl]-5-[(3-carboxamido-4-benzyloxy)benzoyl]pyrrolidine trifluoroacetate (VIII) is obtained.

Step 7. Step 7 describes the reduction of ±cis 2-[(3,4-methylenedioxy)phenethyl]-5-[(3-carboxamido-4-benzyloxy)benzoyl]pyrrolidine trifluoroacetate (VIII) to ±cis erythro 2-[(3,4-methylenedioxy)phenethyl]-5-[(3-carboxamido-4-benzyloxy)-α-hydroxybenzyl]pyrrolidine (IX).

Compound (VIII) is reduced to compound (IX) with a metal borohydride, preferably sodium borohydride dissolved in lower alcohol, preferably in ethanol at 0° temperature. The mixture is reacted for 0.5-3 hours and the solvent is removed. The aqueous residue is diluted with base such as sodium carbonate and the product is extracted with an organic solvent, preferably with ethyl acetate. The extract is washed with water, dried over sodium sulfate, purified, and crystallized by the methods known in the art to give ±cis erythro 2-[(3,4-methylenedioxy)phenethyl]-5-[(3-carboxamido-4-benzyloxy)-α-hydroxybenzyl]pyrrolidine (IX).

Step 8. Step 8 describes the conversion of compound (VIII) in which hydroxy group is protected phenolic hydroxyl, for example benzyloxy, to the compound (X) with unprotected hydroxyl.

The reduction is conducted in alcohol, preferably methanol, in the presence of 5-50 wt% of the noble metal catalyst, preferably 5-20% palladium on carbon. Reduction proceeds at temperatures of 10°-36°, preferably at room temperature, and at atmospheric pressure for 1-100 hours. Purification by methods known in the art and recrystallization from a suitable solvent, preferably acetonitrile, gives compound (X) with unprotected hydroxyl group, namely ±cis erythro 2-[(3,4-methylenedioxy)phenethyl]-5-[(3-carboxamido-4hydroxy)-α-hydroxybenzyl]pyrrolidine.

Reaction Scheme 2 illustrates preparation of cis threo ±2-[(3,4-methylenedioxy)phenethyl]-5-[(3-carboxamido-4-hydroxy)-α-hydroxybenzyl]pyrrolidine.

REACTION SCHEME 2

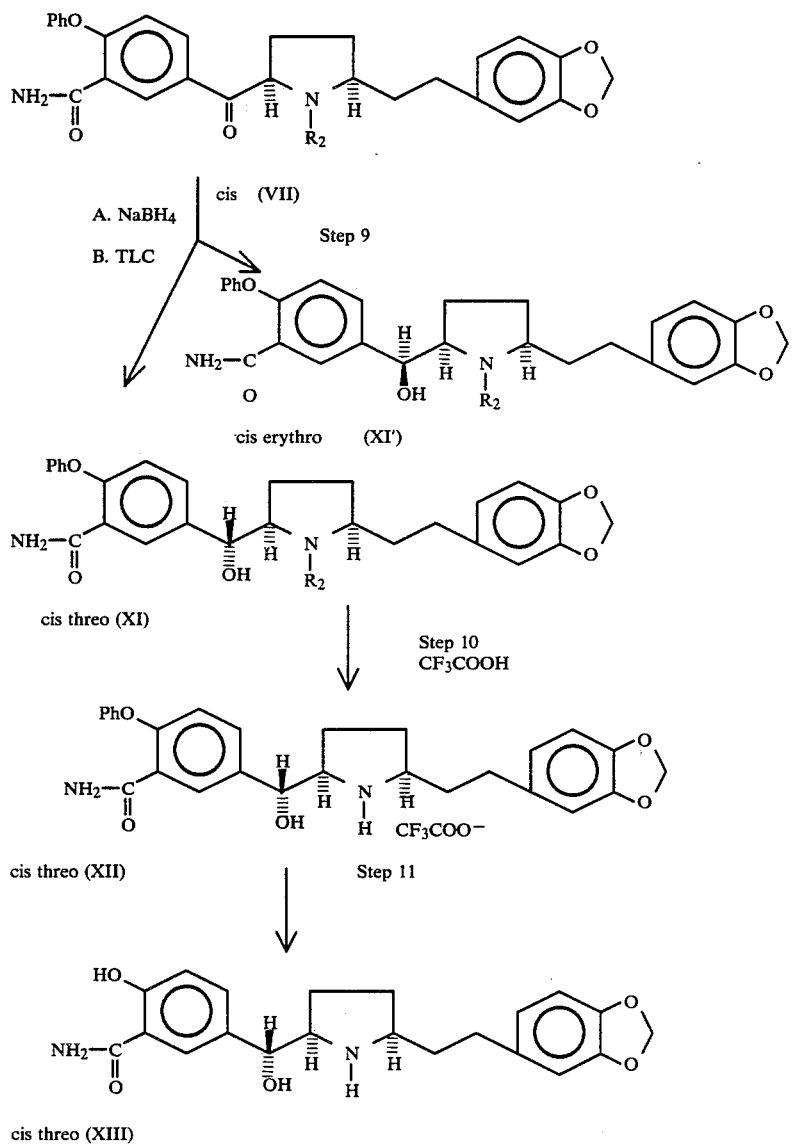

Step 9. Step 9 describes the reduction of keto compound (VII) to the mixture of α-hydroxybenzyl compounds (XI') and (XI), and subsequent separation of the obtained mixture into ±cis erythro isomer (XI') and ±cis threo isomer (XI) of N-protected-2-[(3,4-methylenedioxy)phenethyl]-5-[(3-carboxamido-4-benzyloxy)-α-hydroxybenzyl]pyrrolidine.

Step 9A. ±N-protected cis 2-[(3,4-methylenedioxy)-phenethyl]-5-[(3-carboxamido-4-benzyloxy)benzoyl]-pyrrolidine (VII) (see Reaction Scheme 1) is reduced with metal borohydride, preferably with sodium borohydride, in lower alcohol, preferably ethanol or methanol, at −10 to °20° C., for 0.5–50 hours. The product obtained after purification by methods known in the art is the mixture of both ±cis erythro (XI') and ±cis threo 2-[(3,4-methylenedioxy)phenethyl]-5-[(3-carboxamido-4-benzyloxy)-α-hydroxybenzyl]pyrolidines (XI).

Step 9B. Obtained mixture of cis erythro and cis threo isomers (XI') and (XI) is separated by thin layer chromatography (TLC), column chromatography, crystallization, or any other common separation technique, preferably by TLC, to obtain ±cis erythro 2-[(3,4-methylenedioxy)phenethyl]-5-[(3-carboxamido-4-benzyloxy)-α-hydroxybenzyl]pyrrolidine (XI') and ±cis threo 2-[(3,4-methylenedioxy)phenethyl]-5-[(3-carboxamido-4-benzyloxy)-α-hydroxybenzyl]pyrrolidine (XI).

Cis erythro compound (XI') is then submitted to Step 6 (Reaction Scheme 1) to remove N-protecting group $R_2$.

Step 10. Step 10 describes the removal of the N-protecting group from ±cis threo 2-[(3,4-methylenedioxy)phenethyl]-5-[(3-carboxamido-4-benzyloxy)-α-hydroxybenzyl]pyrrolidine.

A solution of cis threo compound (XI) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain ±cis threo 2-[(3,4-methylenedioxy)phenethyl]-5-[(3-carboxamido-4-benzyloxy)-α-hydroxybenzyl]pyrrolidine trifluoroacetate (XII).

Step 11. Step 1 describes the debenzylation of compound (XII) wherein hydroxy group is protected phenolic hydroxyl, for example benzyloxy, to the compound (XIII).

The reduction is conducted in alcohol, preferably methanol, in the presence of 5-50 wt% of the noble metal catalyst, preferably 5-20% palladium on carbon. Reduction proceeds at temperatures of 10°-36°, preferably at room temperature, and at atmospheric pressure for 1-100 hours. Purification by methods known in the art and recrystallization from a suitable solvent, preferably acetonitrile, gives compound (XIII) with unprotected hydroxyl group.

REACTION SCHEME 3

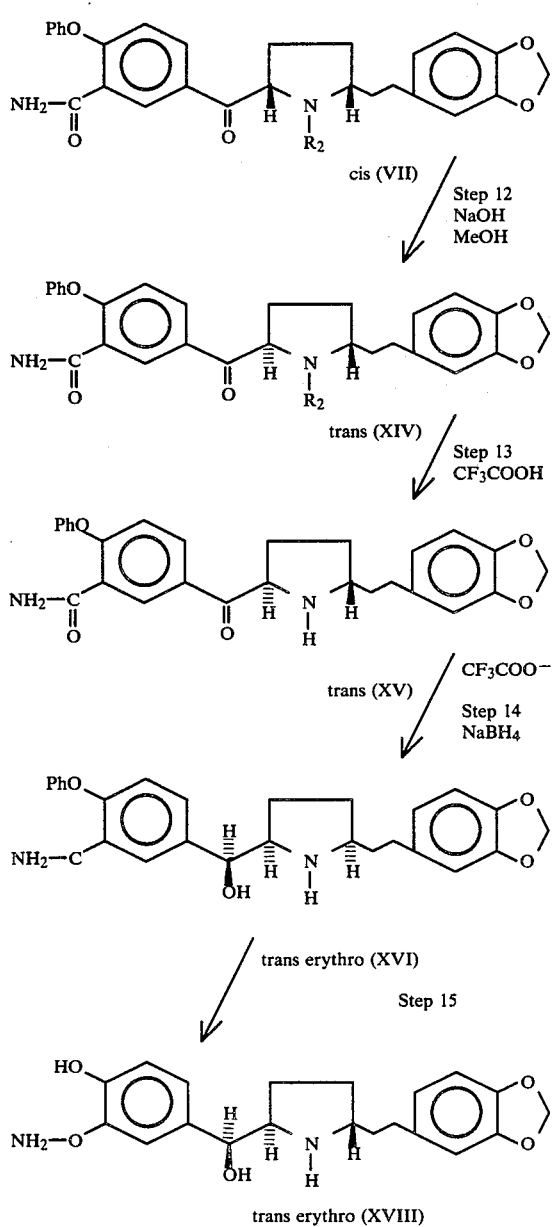

Reaction Scheme 3 illustrates the preparation of ±trans erythro 2-[(3,4-methylenedioxy)phenethyl]-5-[(3-carboxamido-4-hydroxy)-α-hydroxybenzyl]pyrrolidine (XVII).

Step 12. Step 12 illustrates the isomerization of ±cis 2-[(3,4-methylenedioxy)phenethyl]-5-[(3-carboxamido-4-hydroxy)benzoyl]pyrrolidine compound (VII) to the trans 2-[(3,4-methylenedioxy)phenethyl]-5-[(3-carboxamido-4-benzyloxy)benzoyl]pyrrolidine compound (XIV).

±Cis-2-[(3,4-methylenedioxy)phenethyl]-5-[(3-carboxamido-4-benzyloxy)benzoyl]pyrrolidine is dissolved in higher alcohol, for example, propanol, butanol, heptanol, pentanol, preferably in t-butanol and potassium in higher alcohol, preferably in t-butanol is added. The mixture is reacted for 1-6 hours, preferably for 2 hours at a temperature of 10°-30°, preferably at room temperature. The mixture is quenched with ammonium salt, preferably with saturated ammonium chloride, poured in the water and extracted with organic solvent, preferably with ethyl acetate. Purification and crystallization of methods known in the art gave the mixture rich in the ±trans isomer 2-[(3,4-methylenedioxy)phenethyl]-5-[(3-carboxamido-4-benzyloxy)benzoyl]pyrrolidine (XIV).

Step 13. Step 13 describes the removal of the N-protecting group from ±trans 2-[(3,4-methylenedioxy)phenethyl]-5-[(3-carboxamido-4-benzyloxy)benzoyl]pyrrolidine.

A solution of trans compound (XIV), is added to a strong protic acid, such as hydrochloric acid or hydrobromic acid, preferably to 1 ml of trifluoroacetic acid cooled on ice. The mixture is reacted for 1 minute to 5 hours at −10° to +20° C. temperature. The solvent is evaporated and the residue is purified to obtain ±trans 2-[(3,4-methylenedioxy)phenethyl]-5-[(3-carboxamido-4-benzyloxy)benzoyl]pyrrolidine trifluoroacetate (XV).

Step 14. Step 14 describes the reduction of ±trans 2-[(3,4-methylenedioxy)phenethyl]-5-[(3-carboxamido-4-benzyloxy)benzoyl]pyrrolidine compound (XV) to ±trans erythro 2-[(3,4-methylenedioxy)phenethyl]-5-[(3-carboxamido-4-benzyloxy)-α-hydroxybenzyl]pyrrolidine (XVI).

±Trans 2-[(3,4-methylenedioxy)phenethyl]-5-[(3-carboxamido-4-benzyloxy)benzoyl]pyrrolidine trifluoroacetate (XV) is reduced with metal borohydride, preferably with sodium borohydride, in a lower alcohol, preferably ethanol or methanol, at −35° to 10° C. The solution is evaporated and the residue is stirred with the solution of an organic solvent, preferably ethyl acetate, and water. The organic layer is evaporated and the residue dissolved in lower alcohol, such as methanol, ethanol, propanol, butanol, preferably in methanol, and acidified with a solution of hydrogen chloride in the same solvent as above, i.e., preferably in methanol to afford ±trans erythro 2-[(3,4-methylenedioxy)phenethyl]-5-[(3-carboxamido-4-benzyloxy)-α-hydroxybenzyl]pyrrolidine compound (XVI).

Step 15. Step 15 describes the debenzylation of compound (XVI) with protected phenolic hydroxyl, for example benzyloxy, to the compound (XVII) where hydroxyl is unprotected.

The reduction is conducted in alcohol, preferably methanol, in the presence of 5-50 wt% of the noble metal catalyst, preferably 5-20% palladium on carbon, in a hydrogen atmosphere. Reduction proceeds at temperatures of 10°-36°, preferably at room temperature, and at atmospheric pressure for 1-100 hours. Purification by methods known in the art and recrystallization from a suitable solvent, preferably acetonitrile, gives compound (XVII) with unprotected phenolic hydroxyl group, namely, ±trans erythro 2-[(3,4-methylenedioxy)phenethyl]-5-[(3-carboxamido-4-hydroxy)-α-hydroxybenzyl]pyrrolidine compound (XVI).

carboxamido-4-benzyloxy)-α-hydroxybenzyl]pyrrolidine compounds (XVIII) and (XIX).

Step 16B. The mixture obtained in Step 16A is separated by TLC, column chromatography, crystallization or any other common separation technique, preferably by TLC, to obtain ±trans erythro 2-[(3,4-methylenedi-

REACTION SCHEME 4

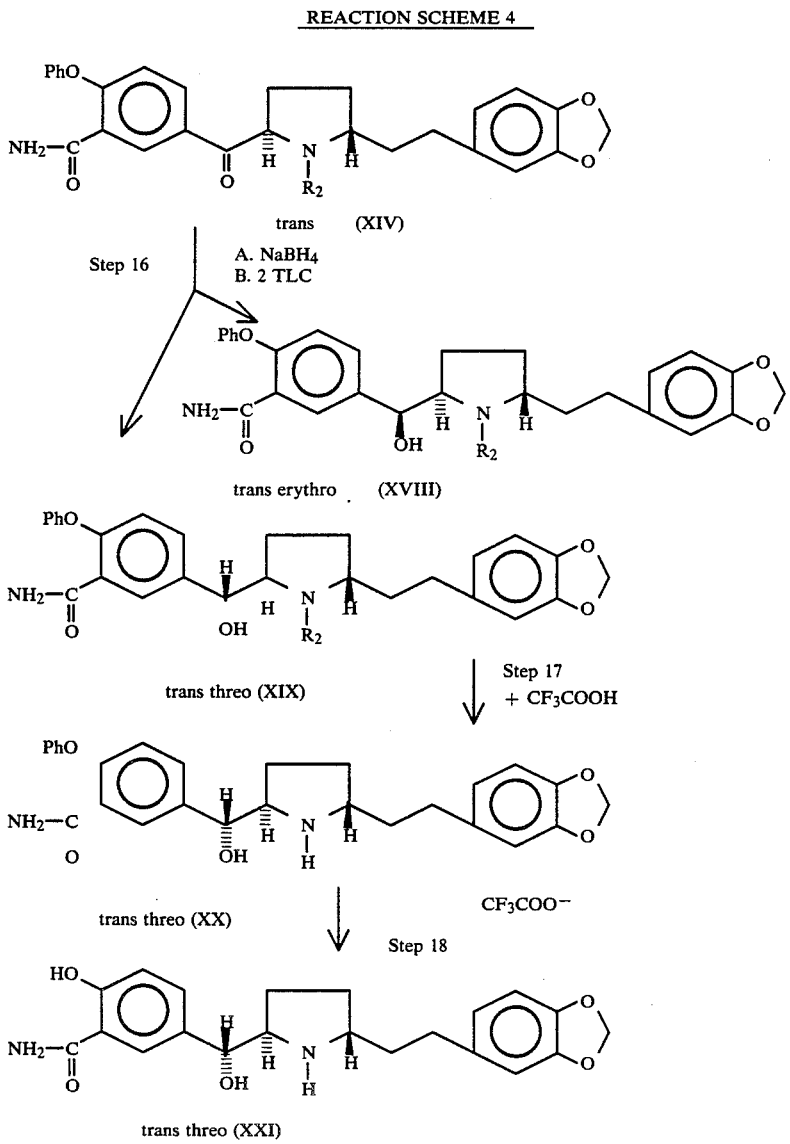

Step 16. Step 16 describes the reduction of N-protected ±trans 2-[(3,4-methylenedioxy)phenethyl]-5-[(3-carboxamido-4-benzyloxy)benzoyl]pyrrolidine compound (XIV) into the N-protected ±trans erythro 2-[(3,4-methylenedioxy)phenethyl]-5-[(3-carboxamido-4-benzyloxy)-α-hydroxybenzyl]pyrrolidine (XVIII) and ±trans threo 2-[(3,4-methylenedioxy)phenethyl]-5-[(3-carboxamido-4-benzyloxy)-α-hydroxybenzyl]pyrrolidine (XIX).

Step 16A. The reaction begins with the reduction of compound (XIV) with metal borohydride, preferably with sodium borohydride, in lower alcohol, preferably ethanol or methanol, at −10° to +20° C. for 0.5-50 hours. The mixture obtained after purification by methods known in the art consist of both ±trans erythro and ±trans threo 2-[(3,4-methylenedioxy)phenethyl]-5-[(3- oxy)phenethyl]-5-[(3-carboxamido-4-benzyloxy)-α-hydroxybenzyl]pyrrolidine (XVIII) and ±trans threo 2-[(3,4-methylenedioxy)0henethyl]-5-[(3-carboxamido-4-benzyloxy)-α-hydroxybenzyl]pyrrolidine (XIX).

N-protected ±trans erythro 2-[(3,4-methylenedioxy)phenethyl]-5-[(3-carboxamido-4-benzyloxy)-αhydroxybenzyl]pyrrolidine (XVIII) is submitted to the procedure of Step 13 (Reaction Scheme 3).

Step 17. Step 17 describes the removal of the N-protecting group from the ±trans threo 2-[(3,4-methylenedioxy)phenethyl]-5-[(3-carboxamido-4-benzyloxy)-αhydroxybenzyl]pyrrolidine compound (XIX).

A solution of ±N-protected trans 2-[(3,4-methylenedioxy)phenethyl]-5-[(3-carboxamido-4-hydroxy)-α-hydroxybenzyl]pyrrolidine compound (XIX) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain the trifluoroacetic acid salt of ±trans threo 2-[(3,4-methylenedioxy)phenethyl]-5-[(3-carboxamido-4-benzyloxy)-α-hydroxybenzyl]pyrrolidine (XX).

Step 18. Step 18 describes the debenzylation of compound (XX) with protected phenolic hydroxyl, for example benzyloxy, to the compound (XXI).

The reduction is conducted in alcohol, preferably methanol, in the presence of 5–50 wt% of the noble metal catalyst, preferably 5–20% palladium on carbon. Reduction proceeds at temperatures of 10°–36°, preferably at room temperature, and at atmospheric pressure for 1–100 hours. Purification by methods known in the art and recrystallization from a suitable solvent, preferably acetonitrile, gives compound (XXI) with unprotected phenolic hydroxyl group, namely ±trans threo 2-[(3,4-methylenedioxy)phenethyl]-5-[(3-carboxamido-4-hydroxy)-α-hydroxybenzyl]pyrrolidine.

Isolation, Separation, and Purification

Isolation, separation, and purification of the desired final compounds and their intermediates from the reaction mixture can be effected by any suitable separation or purification procedure, such as, for example, extraction, filtration, evaporation, distillation, crystallization, thin-layer chromatography, column chromatography, high pressure liquid chromatography, and the like, or by a combination of these procedures. If not otherwise described above, illustrations of suitable isolation, separation and purification procedures can be had by reference to the Examples herein below. However, other isolation, separation and isolation procedures could, of course, also be used.

UTILITY AND ADMINISTRATION

Utility

Applicants have found that certain ±2-[(3,4-methylenedioxy)phenethyl]-5-[(3-carboxamido-4-hydroxy)-αhydroxybenzyl]pyrrolidines are useful for decreasing intraocular pressure when applied topically to the eye. Hence, these compounds are useful for treatment, prevention or inhibition of primary or secondary glaucoma or any other ophthalmic disease which is associated with, or caused by, ocular hypertension.

When compared to other known intraocular pressure lowering agents, compounds of the current invention offer several following advantages:
they are non-irritating to the eye;
they have long duration effect;
they have high efficacy in relatively small doses when administered topically;
they do not cause the secondary side effects observed during the treatment of ocular hypertension.

The ability of compounds of this invention to decrease intraocular pressure is comparable to, or better than that of, timolol maleate, a drug commonly used as topical intraocular hypotensive, without, at the same time, causing undesirable side effects. For example, timolol maleate, when applied topically may be absorbed systemically and can cause bronchospastic disease, bradyarrhythmia, cardiogenic shock, cardiac failure, etc. PDR, 36th Ed., pp. 1284 (1982) *PDR for Ophthalmology*, 11th Ed., pp. 126–127, (1983). To the contrary, compounds of this invention when applied topically are not absorbed systemically and show no systemic activity.

Glaucoma is a group of ocular diseases with common features of abnormally elevated intraocular pressure which slowly causes progressive loss of peripheral visual fields. When untreated, glaucoma causes a loss of central vision and ultimate blindness. A number of diverse clinical cases are included in the category of glaucoma. The causes of the development of glaucoma are mostly unknown. Glaucoma is usually treated topically by agents which constrict the pupil of the eye, such as pilocarpine or carbachol, systemically by osmotic agents or carbonic anhydrase inhibitors, or by surgery. *The Merck Manual*, 13th Ed., 1702, (1977).

To define glaucoma in its simplest form, one can state that there is an intraocular pressure elevation which rests upon an imbalance between aqueous inflow and outflow. The etiology of this imbalance is highly variable.

The glaucoma is generally categorized as primary, secondary, congenital and absolute, and these categories are described in detail in *The Merck Manual* cited above.

It is to be understood that all categories of glaucoma are covered by this invention and will effectively respond to treating with one or more compounds of this invention.

Primary glaucoma is generally sub-classified into two categories, chronic simple (open-angle) glaucoma and acute or chronic congestive (angle-closure) glaucoma.

Presently predominant medical treatment of all types of primary glaucoma (simple open-angle, acute angle-closure and chronic glaucoma) is a topical administration of pilocarpine, timolol maleate, or cholinesterase inhibitors including eserine. The goal of this therapy is to lower the intraocular pressure. Other systemic medications such as acetazolamide, an enzyme inhibitor which acts specifically on carbonic anhydrases, are available for treatment of glaucoma. In the eye, inhibitory action of acetazolamide decreases the secretion of aqueous humor and results in a drop in intraocular pressure, a reaction considered desirable in cases of glaucoma. Other forms of glaucoma may be treated similarly, i.e. by topical administration of pilocarpine, eserine, timolol maleate, corticosteroids or anti-inflammatory agents, or systemically by carbonic anhydrase inhibitors. All forms of glaucoma may be treated surgically. *PDR*, 36th Ed., 1046, (1982).

The goal of topical and systemic therapy of glaucoma is permanent decrease of intraocular pressure. Existing therapy, especially topical therapy with pilocarpine, eserine or timolol, however, require the strong, high percentage topical drops which can be applied only for short time periods. Long treatment with such strong solutions is eye irritating and causes undesirable secondary side effects because many of the topically used drugs are also systemically active.

The compounds of this invention and their pharmaceutically acceptable non-toxic salts have been found, in animal experiments, to be non-irritating, hence physiologically compatible, and yet to have a profound hypotensive effect on intraocular pressure when applied topically directly to the eye. Thus, these compounds are highly potent in penetrating ocular tissue but, surprisingly, upon their topical application, they are not absorbed into systemic circulation and they show no irritation of the ocular tissue. Accordingly, these compounds, when applied topically, offer a method for treating ocular disorders caused or associated with intraocular hypertension of the mammal without exposing the mammal to undesirable secondary symptoms caused by large dosages required for systemic treatment.

The method of this invention is both curative and preventative. Where applied, for example, to the eye which is showing an acute intraocular pressure deviation but is not as yet diagnosed as glaucoma or other ophthalmic disease, it will decrease the elevated intraocular pressure to its normal level and will stabilize it, thus preventing the development of glaucoma. A topical application of appropriate ophthalmic solution with the compound of this invention as an active ingredient to the eye already suffering from increased intraocular pressure will stop a further increase in intraocular pressure and further deterioration of vision. It will also decrease previously elevated pressure to its normal level without submitting the patient to severe secondary symptoms which for example, may occur upon topical administration of timolol maleate.

Administration

The human eye is an excellent subject for the topical administration of drugs. The basis of this can be found in the anatomical arrangement of the surface tissues and in the permeability of the cornea. The protective operation of the eyelids and lacrimal system is such that, unless the material is chemically and physiologically compatible with surface tissues, there is rapid removal of material instilled into the eye.

The therapeutic effect of many topically administered (instilled) drugs is contingent upon their absorption from the cul-de-sac into the eye. Drugs which are administered by instillation and which must penetrate into the eye enter primarily through the cornea. This is a much more effective route of administering the drug into the eye than through the conjunctiva and underlying sclera.

The conjunctiva contains many blood vessels and lymphatic vessels. The blood vessels usually dilate when irritation is set up by a foreign body, a microbial infection, or by chemical means. Of the drug molecules which penetrate into the conjunctiva a large proportion may enter the blood stream where they may cause undesirable systemic reactions. It is, therefore, important that the administered drug have no systemic activity or that it is not absorbed into the blood stream.

In the non-inflamed eye, as for example in glaucoma, the blood-aqueous barrier, constituted of the blood vessel wall and various thicknesses of the ocular tissues, prevents certain systemically administered drugs in therapeutic concentrations from reaching the anterior segment.

In the practice, the compounds of the invention or their pharmaceutically acceptable non-toxic esters and salt are administered topically, i.e., directly to the eye of a subject suffering from glaucoma or ocular hypertension. Administration of the drug is in the form of ophthalmic preparation applied directly to the eye.

Pharmaceutical Composition

Ophthalmic preparations are sterile products for either topical application to the eyelids or instillation into the space (cul-de-sac) between the eyeball and the eyelids. Presently available ophthalmic preparations include solutions, suspensions, and ointments. Presently available topical treatment of eye diseases include topically applied ophthalmic drops, solutions, suspensions or ointment of their subconjunctival injection.

The composition of this invention comprises, as an active ingredient, a compound of this invention or a salt thereof in admixture with an ophthalmologically acceptable excipient.

An excipient is ophthalmologically acceptable if it is non-irritating. It is advantageous if it enables the active ingredient to penetrate the blood-aqueous barrier and/or to diffuse to or through the various ocular substructures to the site where it is pharmacologically active.

The ophthalmic composition may be aqueous or non-aqueous, and it may be in the form of a solution, suspension, gel, ointment, slow release polymer, or other. Amount of active ingredient will vary with the particular formulation and disease state but generally will be between 0.001–10% wt/vol of active ingredient per individual application dose.

Pharmaceutical ophthalmic compositions are typically sterilized aqueous solutions (i.e. eyedrops) containing 0.001% to 10% wt/vol.; most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives/sterilants are phenylmercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, typical dosage ranges might be about 2–10 drops of 0.1% solution of active ingredient once to three times per day.

Most ophthalmic solutions and suspensions contain an aqueous rather than an oily vehicle. Ophthalmic ointments usually contain a white petrolatum-mineral oil base, often including anhydrous lanolin, while some have a polyethylene-gelled mineral oil base.

Solutions are the most commonly used type of preparation for the local medication of eyes. They are easily instilled and rarely cause adverse reactions. The vehicle does not cause interference with vision and does not interfere with regeneration of the corneal epithelium.

Oily solutions such as for medicaments which are incompatible with water are infrequently used. The only official ophthalmic solution using oil is that of isoflurophate.

Suspensions have the advantage of more extended action and the disadvantage that it is difficult to avoid the presence of a few particles which are large enough to cause irritation.

Eye ointments are sterile preparations for application to the conjunctival sac or lid margin. They have advantages of more prolonged contact and effect, hardly any irritation on initial installation, slower movement into lacrimal ducts, greater storage stability, and less likelihood of contamination problems. Their disadvantages are that they produce a film over the eye and thereby blur vision; and they may interfere with the firm attachment of new corneal epithelial cells to their normal base. Ointments affect the outside and edges of the eyelids, the conjunctiva, the cornea, and the iris, depending on their ability to penetrate the outer covering of the eyeball.

Ophthalmic ointments comprising active ingredients can be used for the effect of a variety of medicaments on the outside and edges of the eyelids, the conjunctiva, the cornea, and the iris. Most ophthalmic ointments are prepared with a base of white or yellow petrolatum and mineral oil, often with added anhydrous lanolin. Whichever base is selected, it must be nonirritating to the eye, permit diffusion of the drug throughout the secretions bathing the eye, and retain the activity of the medicament for a reasonable period of time under proper storage conditions.

Compounds of this invention may also be administered by other nonsystemic modes. Ophthalmic packs may be used to give prolonged contact of the solution with the eye. A cotton pledget is saturated with an ophthalmologically suitable solution and this pledget is inserted into the superior or inferior fornix. Packs are commonly used to produce maximal mydriasis. In this case the cotton pledgets can be, for example, saturated with a solution of a compound of this invention. Medicated ophthalmic disks produce mitosis both more intense and prolonged than either solution. Use of disks may be preferable to use of solutions.

The compounds may also be administered by the way of iontophoresis. This procedure keeps the solution in contact with the cornea in an eyecup bearing an electrode. Diffusion of the drug is effected by difference of electrical potential.

Subconjunctival injections of compounds of the current invention may be used to introduce medications which, if instilled, either do not penetrate into the anterior segment or penetrate too slowly for the desired effect. The conjunctival membrane covers the outer surface of the white portion of the eye and the inner aspect of the eyelids. In most places it is loosely attached and thereby permits free movement of the eyeball. This makes possible subconjunctival injections. The drug is injected underneath the conjunctiva and propably passes through the sclera and into the eye by simple diffusion. The most common use of subconjunctival injection is for the administration of antibiotics in infections of the anterior segment of the eye. Subconjunctival injections of mydriatics and cycloplegics are also used to achieve maximal pupillary dilation or relaxation of the ciliary muscle. If the drug is injected underneath the conjunctiva and the underlying Tenon's capsule in the more posterior portion of the eye, effects on the ciliary body, choroid, and retina can be obtained.

Drugs may also be administered by retrobulbar injection whereby they enter the globe in essentially the same manner as the medications given subconjunctivally. The orbit is not well vascularized and the possibility of significant via blood stream effects of retrobulbar injections is very remote. In general, retrobulbar injections are given for the purpose of getting medications into the posterior segment of the globe and to affect the nerves and other structures in the retrobulbar space. *Remington's Pharmaceutical Sciences*, 15th Ed., 1489-1504, (1975).

The following examples are intended to illustrate, but not to limit, the scope of the invention.

EXAMPLE 1

Preparation of [(3-Carboxamido-4-Benzyloxy)Benzoyl]Morpholide (I)

This example illustrates the preparation of [(3-carboxamido-4-benzyloxy)benzoyl]morpholide. This compound can be prepared from the corresponding (3-carboxamido-4-hydroxy)benzoic acid by protecting the phenolic hydroxy group.

A. Methyl ester (3-carboxamido-4-hydroxy)benzoic acid was prepared according to the procedure described in *J. Chem. Soc.*, pp. 4678 (1956). The procedure is also described in Brit. Pat. No. 802,841.

B. Methyl ester(3-carboxamido-4-hydroxy)benzoic acid is dissolved in dimethylformamide (10 ml/mmol) and treated with 1 equivalent of sodium hydride at room temperature under constant stirring for about 5 minutes. Then 1 equivalent of benzyl bromide is added and the mixture is stirred at room temperature until reaction is complete, usually for 1 hour. The mixture is poured into water and extracted with ethyl acetate. The extract is washed with water to eliminate dimethylformamide, evaporated in vacuo to afford methyl ester (3-carboxamido-4-benzyloxy)benzoic acid. Methyl ester (3-carboxamido-4-benzyloxy)benzoic acid is hydrolyzed to benzoic acid with bicarbonate in methanol for about 12 hours to give (3-carboxamido-4-benzyloxy)-benzoic acid.

C. To a suspension of 11.5 g of (3-carboxamido-4-benzyloxy)benzoic acid in 250 ml of dichloromethane was added 2.87 ml of thionyl chloride and 1 ml of dimethylformamide. The mixture is stirred at room temperature for approximately 15 min. or until solution occurred. The solvent was removed in vacuo. The residual acid chloride was dissolved in ether, and 5.8 ml of morpholine was added slowly with stirring. The precipitate was removed by filtration. The ether was evaporated in vacuo to give 11.4 g of an oil which was purified by column chromatography in silica gel with ethyl acetate-hexane (2:3) as the eluting solvent to give in [(3-carboxamido-4-benzyloxy)benzoyl]morpholide (I). (Step 3)

EXAMPLE 2

Preparation of [(3,4-Methylenedioxy)Phenylacetyl]Morpholide (IIa)

4 ml of thionyl chloride and 0.5 ml of dry dimethylformamide were added to a solution of 12.5 g of (3,4-methylenedioxy)phenylacetic acid (Trans World Chemical) in 200 ml of dry dichloromethane. The solution was stirred for 15 minutes and evaporated to dryness in vacuo. The residual acid chloride was dissolved in 100 ml of dry dichloromethane. A solution of 5.35 ml of morpholine in 100 of dichloromethane was added dropwise with stirring. When the addition was ended, the mixture was evaporated to dryness in vacuo and the residue was percolated through a short silica gel column using ethyl acetate-hexane (3:7) as the percolating solvent. 13.7 g of [(3,4-methylenedioxy)phenylacetyl]-morpholide (IIa) was obtained. (Step 1)

EXAMPLE 3

Preparation of 2-[(3,4-Methylenedioxy)Phenylacetyl]Pyrrole (III)

Vilsmeier-Haack reaction was carried out according to the method of J. White and G. McGillivray, *J. Org. Chem.*, 42:4248 (1979).

A mixture of 30 g (0.146 mole) of [(3,4-methylenedioxy)phenylacetyl]morpholide and 27 ml (0.295 mole) of phosphorous oxychloride was stirred magnetically at room temperature in a nitrogen atmosphere for 6 h. A solution of 10 ml (0.149 mole) of pyrrole in 700 ml of anhydrous 1,2-dichloroethane was added at a rate such that the temperature did not exceed 30°. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was subjected to column chromatography over silica gel (1 kg). 2-[(3,4-methylenedioxy)phenylacetyl]pyrrole (III) was eluted with dichloromethane and crystallized from acetone-hexane. (Step 1)

EXAMPLE 4

Preparation of
2-[(3,4-Methylenedioxy)Phenethyl]Pyrrole (IV)

A solution of 6.00 g (0.032 mole) of the 2-[(3,4-methylenedioxy)phenylacetyl]pyrrole (III) in 200 ml of anhydrous tetrahydrofuran was added to a suspension of 600 g (0.153 mole) of lithium aluminum hydride in dry tetrahydrofuran. The mixture was stirred at reflux temperature for 48 h. The mixture was cooled to 0°, and ethyl acetate was cautiously added to destroy the excess hydride. Then the saturated aqueous sodium sulfate was added, the organic phase was decanted, dried over sodium sulfate and evaporated in vacuo. The residue was subjected to column chromatography on neutral alumina (Fluka, Act II). 2-[(3,4-methylenedioxy)phenethyl]pyrrole (IV) was eluted with hexane-ethyl acetate and crystallized from (hexane). (Step 2).

EXAMPLE 5

Preparation of
±2-[(3,4-Methylenedioxy)Phenethyl]-5-[(3-Carboxamido-4-Benzyloxy)Benzoyl]Pyrrole (V)

A mixture of 12,3 g (0.046 mole) of [(3-carboxamido-4-benzyloxy)benzoyl]morpholide (I) (Example 1) and 12 ml (0.13 mole) of phosphorous oxychloride was stirred at room temperature for 3 hours in a nitrogen atmosphere. A solution of 10.0 g (0.058 mole) of 2-[(3,4-methylenedioxy)phenethyl]pyrrole (IV) in 200 ml of dry 1,2-dichloroethane was added and the mixture was stirred at room temperature for 18 h. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was submitted to column chromatography on neutral alumina (Fluka, Act II). The crude product was purified by column chromatography on silica gel (1 kg). The desired material was eluted with dichloromethane to give ±2-[(3,4-methylenedioxy)phenethyl]-5-[(3-carboxamido-4-benzyloxy)benzoyl]pyrrole (V) which was crystallized from dichloromethane-acetone. (Step 3)

EXAMPLE 6

Preparation of
1-t-Butoxycarbonyl-2-[(3,4-Methylenedioxy)Phenethyl]-5-[(3-Carboxamido-4-Benzyloxy)Benzoyl]Pyrrole (VI)

4.10 g (0.012 mole) of ±2-[(3,4-methylenedioxy)phenethyl]-5-[(3-carboxamido-4-benzyloxy)benzoyl]pyrrole (V) was added to a 1.40 g of suspension (0.50 mole; 60% dispersion in mineral oil) of sodium hydride in 100 ml of dry dimethylformamide. The mixture was heated at 45°-60° for 2 h. 4.51 g (0.02 mole) of di-t-butyl dicarbonate was added rapidly and the solution was stirred at 60°-70° for 2 h. The reaction mixture was cooled, poured onto ice-water and the product was extracted into ethyl acetate. The extract was washed with water, dried over sodium sulfate and evaporated in vacuo. Then it was purified by column chromatography on alumina (300 g, Fluka, Neutral Act. II). The crude product was crystallized from acetone-hexane to give ±1-t-butoxycarbonyl-2-[(3,4-methylenedioxy)phenethyl]-5-[(3-carboxamido-4-benzyloxy)benzoyl]pyrrole (VI). (Step 4)

EXAMPLE 7

Preparation of ±Cis 1-t-Butoxycarbonyl
2-[(3,4-Methylenedioxy)Phenylethyl]-5-[(3-Carboxamido-4-Benzyloxy)Benzoyl]Pyrrolidine (VII)

A solution of 4.50 g, (0.01 mole) 1-t-butoxycarbonyl-2-[(3,4-methylenedioxy)phenethyl]-5-[(3-carboxamido-4-benzyloxy)benzoyl]pyrrole (VI) in 300 ml of ethyl acetate (2:1) containing 1.8 g of suspended platinum on carbon was hydrogenated at room temperature and atmospheric pressure for 22 hours. The reaction mixture was filtered, the filtrate was evaporated in vacuo and the residue was subjected to column chromatography on neutral alumina (Fluka, Act II). The product was eluted with hexane-ethyl acetate (95:5). The crude ±cis 1-t-butoxycarbonyl 2-[(3,4-methylenedioxy)phenethyl]-5-[(3-carboxamido-4-benzyloxy)benzoyl]pyrrolidine (VII) was obtained in quantitative yield as an oil. (Step 5)

The above hydrogenation procedure, however, may result in partial or complete debenzylation of phenolic hydroxyl. If such is the case the phenolic hydroxyl must be again protected by benzylation. The process of benzylation has been described in Example 1.

EXAMPLE 8

Preparation of ±Cis
2-[(3,4-Methylenedioxy)Phenethyl]-5-[(3-Carboxamido-4-Benzyloxy)Benzoyl]Pyrrolidine
Trifluoroacetate (VIII)

50 ml of trifluoroacetic acid was added to a solution of 3.60 g (0.0085 mole) of ±cis 1-t-butoxycarbonyl-2-[(3,4-methylenedioxy)phenethyl]-5-[(3-carboxamido-4-benzyloxy)benzoyl]pyrrolidine (VII) in 200 ml of dry dichloromethane. The reaction solution was stirred at room temperature for 0.5 h. The solvent was removed in vacuo and the residue was crystallized from dichloromethane-ether to give ±cis 2-[(3,4-methylenedioxy)phenethyl]-5-[(3-carboxamido-4-benzyloxy)benzoyl]pyrrolidine trifluoroacetate (VIII) (Step 6).

EXAMPLE 9

Preparation of ±Cis Erythro 2-[(3,4-Methylenedioxy)Phenethyl]-5-[(3-Carboxamido-4-Benzyloxy)-α-Hydroxybenzyl]Pyrrolidine (IX)

1.35 g (0.035 mole) of sodium borohydride was added to a stirred solution of 2.70 g (0.0057 mole) of ±cis 2-[(3,4-methylenedioxy)phenethyl]-5-[(3-carboxamido-4-benzyloxy)-α-hydroxybenzyl]pyrrolidine in 270 ml ethanol, at 0° temperature. After 1 hour at 0°, the mixture was poured into 100 ml of 10% ammonium chloride solution. The mixture was evaporated in vacuo to remove the ethanol, the residue was cooled to 0°, and 50 ml of a saturated sodium carbonate solution was added. The product was extracted into ethyl acetate, the extract was washed with water, dried over sodium sulfate and evaporated in vacuo. The residue was crystallized from ethyl acetate-hexane to give 1.72 g (93%) of the desired ±cis erythro 2-[(3,4-methylenedioxy)phenethyl]-5-[(3-carboxamido-4-benzyloxy)-α-hydroxybenzyl]pyrrolidine (IX). (Step 7)

EXAMPLE 10

Debenzylation of ±Cis Erythro 2-[(3,4-Methylenedioxy)Phenethyl]-5-[(3-Carboxamido-4-Benzyloxy)-α-Hydroxybenzyl]Pyrrolidine A solution of the ±cis erythro 2-[(3,4-methylenedioxy)phenethyl]-5-[(3-carboxamido-4-benzyloxy)-α-hydroxybenzyl]pyrrolidine (0.600 g 0.0012 mole) in absolute methanol (20 ml) containing suspended 10% palladium on carbon catalyst (0.30 g) was hydrogenated at room temperature and atmospheric pressure for 1 hour. The mixture was filtered through Celite, the filtrate was evaporated in vacuo and the residue was triturated with acetone and crystallized from methanol-acetone, to give ±cis erythro 2-[3,4-methylenedioxy)-phenethyl]-5-[(3-carboxamido-4-hydroxy)α-hydroxybenzyl]pyrrolidine, m.p. 189–191.

Other compounds may be similarly debenzylated:

±trans erythro 2-[3,4-methylenedioxy)phenethyl]-5-[(3-carboxamido-4-hydroxy)α-hydroxybenzyl]pyrrolidine, m.p. 189–191.

±cis threo 2-[3,4-methylenedioxy)phenethyl]-5-[(3-carboxamido-4-hydroxy)α-hydroxybenzyl]pyrrolidine, m.p. 193–193.5.

EXAMPLE 11

A. Preparation of ±Cis Erythro and ±Cis Threo 1-t-Butoxycarbonyl-2-[(3,4-Methylenedioxy)Phenethyl]-5-[(3-Carboxamido-4-Benzyloxy)α-Hydroxybenzyl]Pyrrolidine (XI') and (XI)

A solution of 3.20 g (4.5 mmole) of the ±cis 1-t-butoxycarbonyl-2[(3,4-methylenedioxy)phenethyl]-5-[(3-carboxamido-4-benzyloxy)benzoyl]pyrrolidine (VII), prepared in Example 7 and 6.4 g (16.9 mmole) of sodium borohydride in 300 ml ethanol is heated at a reflux temperature for 45 min. The solvent is removed in vacuo and the residue is partitioned btween water and ethyl acetate. The organic phase is evaporated in vacuo and the residue is percolated through a short column of silica gel using ethyl acetate-hexane (1:3) as the percolating solvent.

The resulting mixture is separated by TLC with ethyl acetate/hexane (1:3) into two isomers:

±cis erythro 1-t-butoxycarbonyl 2-[(3,4-methylenedioxy)phenethyl]-5-[(3-carboxamido-4-benzyloxy)-α-hydroxybenzyl]pyrrolidine; and ±cis threo 1-t-butoxycarbonyl 2-[(3,4-methylenedioxy)phenethyl]-5-[(3-carboxamido-4-benzyloxy)-α-hydroxybenzyl]pyrrolidine.

B. Preparation of ±Trans Erythro and ±Trans Threo 1-t-Butoxycarbonyl-2-[(3,4-Methylenedioxy)Phenethyl]-5-[(3-Carboxamido-4-Benzyloxy)α-Hydroxybenzyl]Pyrrolidine (XI') and (XI)

The same procedure as described in Section A is used for the preparation of ±trans erythro (XVIII) and ±trans threo (XIX) compounds shown in Reaction Scheme 4 (Step 16) except that the starting compound is a trans isomer (XIV).

The resulting compounds are:

±trans erythro 1-t-butoxycarbonyl 2-[(3,4-methylenedioxy)phenethyl]-5-[(3-carboxamido-4-benzyloxy)-α-hydroxybenzyl]pyrrolidine, m.p. 115°–116°; and ±trans threo 1-t-butoxycarbonyl 2-[(3,4-methylenedioxy)phenethyl]-5-[(3-carboxamido-4-benzyloxy)-α-hydroxybenzyl]pyrrolidine.

EXAMPLE 12

Removal of N-Protecting Group from ±Cis Erythro or ±Cis Threo 1-t-Butoxycarbonyl-2-[(3,4-Methylenedioxy)Phenethyl]-5-[(3-Carboxamido-4-Benzyloxy)-α-Hydroxybenzyl]Pyrrolidine (XI')(XI)

50 ml of trifluoroacetic acid is added to a solution of ±cis erythro 1-t-butoxycarbonyl 2-[(3,4-methylenedioxy)phenethyl]-5-[(3-carboxamido-4-benzyloxy)-α-hydroxybenzyl]pyrrolidine (XI') or to a solution of 3.60 g (0.0085 mol) ±cis threo 1-t-butoxycarbonyl-2-[(3,4-methylenedioxy)phenethyl]-5-[(3-carboxamido-4-benzyloxy)-α-hydroxybenzyl]pyrrolidine (XI) in 200 ml of dichloromethane. The reaction mixture is stirred at room temperature for 0.5–1 hour. The solvent is removed in vacuo and the residue is crystallized from dichloromethane-ether to give trifluoroacetic acid salt of compounds (XI') and (XI).

Resulting compounds are:

±cis erythro 2-[(3,4-methylenedioxy)phenethyl]-5-[(3-carboxamido-4-benzyloxy)-α-hydroxybenzyl]pyrrolidine trifluoroacetate; and ±cis threo 2-[(3,4-methylenedioxy)phenethyl]-5-[(3-carboxamido-4-hydroxy)-α-hydroxybenzyl]pyrrolidine trifluoroacetate (XII). (Step 10)

The same procedure is used for the removal of N-protecting group from compounds (XIV), (XV), (XVIII) and (XIX), shown in Reaction Schemes 3 and 4.

EXAMPLE 13

Isomerization of ±Cis 1-t-Butyloxycarbonyl-2-[(3,4-Methylenedioxy)Phenethyl]-5-[(3-Carboxamido-4-Benzyloxy)Benzoyl]Pyrrolidine to ±Trans-1-t-Butyloxycarbonyl-2-[(3,4-Methylenedioxy)Phenethyl]-5-[(3-Carboxamide-4-Benzyloxy)Benzoyl]Pyrrolidine 550 mg of ±cis 1-t-butyloxycarbonyl-2-[(3,4-methylenedioxy)phenethyl]-5-[(3-carboxamido-4-benzyloxy)benzoyl]pyrrolidine is dissolved in 50 ml of t-butanol and 1 ml of a solution prepared by dissolving 3-4 g of potassium in 60 ml of t-butanol, is added. After 2 hours at room temperature, the reaction mixture is quenched by adding 1 ml of saturated ammonium chloride. The solution is then poured into water and extracted with ethyl acetate. The ethyl acetate layer is washed, dried and evaporated to yield a residue. The analysis of the residue showed it to be a 50:50 mixture of starting material and a new slightly more polar compound. The more polar compound was isolated by chromatography on silica gel eluting twice with ethyl acetate/hexane (1:2)(2:1) to yield ±trans N-t-butyloxycarbonyl-2-[(3,4-methylenedioxy)phenethyl-5-(3-carboxamido-4-benzyloxy)benzoyl]pyrrolidine, m.p. 115°-116°.

EXAMPLE 14

Conversion of ±Trans 1-t-Butyloxycarbonyl-2-[(3,4-Methylenedioxy)Phenethyl]-5-[(3-Carboxamido-4-Benzyloxy)Benzoyl]Pyrrolidine to ±Trans Erythro 2-[(3,4-Methylenedioxy)Phenethyl]-5-[(3-Carboxamido-4-Benzyloxy)-α-Hydroxybenzyl]Pyrrolidine Hydrochloride 40 mg of ±trans 1-t-butyloxycarbonyl-2-[(3,4-methylenedioxy)phenethyl]-5-[(3-carboxamido-4-benzyloxy)benzoyl]pyrrolidine was dissolved in 1 ml of trifluoroacetic acid cooled on an ice bath. After about 1 minute, the solution was evaporated in vacuo and the residue dissolved in 1 ml of ethanol and added to a solution of 25 mg of sodium borohydride in 5 ml of ethanol cooled to −35°. After warming to room temperature, the solution was evaporated and the residue stirred with ethyl acetate and water. The organic layer was separated, washed, dried, and evaporated to leave a residue which was dissolved in methanol. The solution was acidified with a solution of hydrogen chloride in methanol. The solvent was removed by evaporation and the residue stirred with ethyl acetate to give 28 mg of ±trans erythro-2-[(3,4-methylenedioxy)phenethyl]-5-[(3-carboxamido-4-benzyloxy)-α-hydroxybenzyl]pyrrolidine hydrochloride, m.p. 178°-179°.

EXAMPLE 15

Conversion of ±Trans Erythro 2-[(3,4-Methylenedioxy)Phenethyl]-5-[(3-Carboxamido-4-Benzyloxy)-α-Hydroxybenzyl]Pyrrolidine Hydrochloride to ±Trans Erythro 2-[(3,4-Methylenedioxy)Phenethyl]-5-[(3-Carboxamido-4-Hydroxy)-α-Hydroxybenzyl]Pyrrolidine Hydrochloride 25.9 mg of ±trans erythro 2-[(3,4-methylenedioxy)phenethyl]-5-[(3-carboxamido-4-benzyloxy)-α-hydroxybenzyl]pyrrolidine hydrochloride is dissolved in methanol and 3 mg of 5% palladium on carbon catalyst is added. The mixture is stirred overnight in a hydrogen atmosphere. The solution is filtered, the filtrate evaporated and the residue triturated with ethyl acetate. The ±trans erythro-2-[(3,4-methylenedioxy)phenethyl]-5-[(3-carboxamido-4-hydroxy)-α-hydroxybenzyl]pyrrolidine hydrochloride is collected by filtration and dried. After recrystallization from ethanol it had m.p. 189°-190°.

EXAMPLE 16

Conversion of Free Base to Salt Preparation of ±Cis Erythro 2-[(3,4-Methylenedioxy)Phenethyl]-5-[(3-Carboxamido-4-Hydroxy)-α-Hydroxybenzyl]Pyrrolidine Hydrochloride Excess 3% hydrogen chloride in methanol is added to a solution of 1.0 g of ±cis erythro 2-[(3,4-methylenedioxy)phenethyl]-5-[(3-carboxamido-4-hydroxy)-α-hydroxybenzyl]pyrrolidine in 20 ml of methanol. Diethyl ether is added until precipitation is complete. ±Cis erythro 2-[(3,4-methylenedioxy)phenethyl]-5-[(3-carboxamido-4-hydroxy)-α-hydroxybenzyl]pyrrolidine hydrochloride is filtered, washed with ether, air dried and recrystallized.

Other isomers may be similarly converted to various salts.

EXAMPLE 17

Conversion of Salt to Free Base Preparation of ±Cis Erythro 2-[(3,4-Methylenedioxy)Phenethyl]-5-[(3-Carboxamido-4-Hydroxy)-α-Hydroxybenzyl]Pyrrolidine 1.0 g of ±cis erythro 2-[(3,4-methylenedioxy)phenethyl]-5-[(3-carboxamido-4-hydroxy)-α-hydroxybenzyl]pyrrolidine hydrochloride or trifluoroacetate is dissolved in 50 ml of water. A solution of sodium bicarbonate is added, and the pH adjusted to about pH 5. The resulting free base is extracted with ethyl acetate, the organic layer is then separated, washed twice with water, dried over magnesium sulfate and evaporated to yield ±cis erythro 2-[(3,4-methylenedioxy)phenethyl]-5-[(3-carboxamido-4-hydroxy)-α-hydroxybenzyl)]pyrrolidine as the free base.

EXAMPLE 18

Direct interchange of acid addition salts 1 g of ±cis erythro 2-[(3,4-methylenedioxy)phenethyl]-5-[(3-carboxamido-4-hydroxy)-α-hydroxybenzyl]pyrrolidine hydrochloride, prepared according to Example 13, is dissolved in a solution of 1 ml 50% aqueous sulfuric acid in 10 ml ethanol and the resulting precipitate is harvested. The product is suspended in ethanol and filtered, air dried, and recrystallized from methanol/acetone to yield ±cis erythro 2-[(3,4-methylenedioxy)phenethyl]-5-[(3-carboxamido-4-hydroxy)-α-hydroxybenzyl]pyrrolidine bisulfate.

In Examples 16–23, the active ingredient is ±cis erythro 2-[(3,4-methylenedioxy)phenethyl]-5-[(3-carboxamido-4-hydroxy)-α-hydroxybenzyl]pyrrolidine hydrochloride.

EXAMPLE 19

Eye Irritation Study

This example illustrates non-irritating properties of compounds of this invention when used as topical ocular hypotensive.

To be an effective topical ocular hypotensive agent, the compound must prove itself to be non-irritating. To determine the effects of various compounds on eye irritation, the comparative irritability test among known ocular hypotensives was designed wherein the irritation of the eye following the topical application of tested compound was measured and compared to the irritation of the eye following the application of other ocular hypotensive compound.

Experimental Protocol

Each studied compound was tested individually on a single animal by administering, at the same time, into one eye of the animal the ophthalmic solution with the test compound as an active ingredient and to the other eye only vehicle ophthalmic solution. An irritation, if any, caused by tested compounds was compared to the non-irritating effect of the vehicle ophthalmic solution applied to the other eye. Irritation was measured by the number of blinks of each eye during the same time period. Tests were performed on rats, dogs and monkeys.

Ophthalmic solutions of ±2-[(3,4-methylenedioxy)-phenethyl]-5-[(3-carboxamido-4-hydroxy)-α-hydroxybenzyl]pyrrolidines as the active ingredient were prepared at the concentrations of 0.01% to 0.5%. One drop of the test ophthalmic solution with active ingredient was administered directly into the conjuctival sack of the rat's left eye. At the same time one drop of vehicle was administered to the conjunctival sack of the rat's right eye.

Irritation of each eye was measured by counting the number of blinks for one minute after the application. The results were expressed as the mean number of blinks±standard error per eye. The mean number of blinks/minute were averaged for the vehicle treatment and compared to the drug treated eye. Each compound was tested similarly in mongrel dogs and rhesus monkeys.

Results

The compounds of this invention did not elicit any irritation of the eyes in any of the three species at any concentration which was used for testing (i.e., 0.12–0.5%) and their effects were comparable to the effect of the vehicle ophthalmic solution without any drug added.

EXAMPLE 20

Reduction of Intraocular Pressure

This example illustrates the effect of compounds of the current invention on intraocular pressure (IOP).

Experimental Protocol

Two groups of normal albino white New Zealand rabbits were used for this study.
Control group: 4 animals
Experimental group: 8 animals

Experimental schedule

At time 0, intraocular pressure of both eyes of each animal in control and experimental groups was determined.

All animals received the treatment either with saline (control group) or the tested compound (experimental group) immediately after 0 hour intraocular pressure reading. Control group received 50 μl of vehicle in both eyes. Experimental animals received 50 μl of vehicle in the left eyes and 50 μl of 1% solution of tested compound in the right eyes.

Intraocular pressure was measured at 30 minutes, 1, 2, and 4 hours.

Experimental Procedure

The effects of tested drug on intraocular pressure of the rabbit was determined using a Digilab Model 30D pneuma-tonometer. Initial IOP readings were obtained in all animals after the administration of 50 μl of 0.5% Opthaine (proparacaine hydrochloride). A group of 4 rabbits served as controls and were treated with 50 μl of saline in both eyes. Eight additional rabbits received 50 μl of test drug in the right eye, and 50 μl of drug vehicle was administered in the contralateral left eye. IOP readings were made 30 minutes, 1 hours, 2 hours, and 4 hours after drug administration. Rabbits were observed for any signs of ocular irritation.

This procedure permitted the comparison of drug treated eye with the contralateral vehicle treated eye, and also with saline treated eye. For purposes of statistical analysis comparisons were made between the drug treated IOP values and vehicle treated contralateral eyes and also the saline treated IOP values.

Results

TABLE 1

| Time | Controls (N = 4) | | Experimental (n = 8) | |
|---|---|---|---|---|
| | O.D. | O.S. | O.D. | O.S. |
| 0 | 18.8 | 19 | 17.6 | 18 |
| 30 min | 18.3 | 18.8 | 18.9 | 18.1 |
| 1 hour | 19.5 | 18.5 | 17.1 | 19.8 |
| 2 hours | 19.8 | 18 | 14.4 | 17.3 |
| 4 hours | 19.8 | 18.3 | 15.5 | 18.8 |

O.S. = left eye,
O.D. = right eye

Intraocular pressure is expressed in mmHg.

Each number represents the average of IOP from 4 eyes.

Tested compound was ±2-[(3,4-methylenedioxy)-phenethyl]-5-[(3-carboxamido-4-hydroxy)-α-hydroxybenzyl]pyrrolidine.

Results

Results summarized in Table 1 show that the administration of 1% solution of a tested compound decreased significantly intraocular pressure in the right (treated) eyes of the experimental group.

EXAMPLE 21

Systemic Effect of the Drugs Following the Topical Ocular Administration

Timoptic, a β-blocking agent currently marketed for treating glaucoma, has been shown to be absorbed systemically after ocular application and to intensify cardiac failure in congestive heart failure patients and brochospasm in patients suffering from brochospastic disorders.

In the present studies, the cardiovascular and intraocular pressure effects of Timoptic (Timolol) a Merck β-blocker marketed for treatment of glaucoma, and ±2-[(3,4-methylenedioxy)phenethyl]-5-[(3-carboxamido-4-hydroxy)-α-hydroxybenzyl]pyrrolidine were evaluated in anesthetized dogs to determine if the compounds exert systemic effects after ocular administration.

Experimental Preparation

Mongrel dogs were anesthetized with sodium pentobarbital (36 mg/kg, i.v.). The trachea was intubated and the dog respired with room air if necessary (20 cc/kg, 16x/min). A femoral vein was cannulated for injection of drugs and a femoral artery for measurement of systolic blood pressure. Heart rate was recorded by a cardiotachometer triggered by the R-wave of a limb lead II ECG. Intraocular pressure measurements were made with a Digilab model 30-D Pneuma-Tonometer.

Timolol and ±2-[(3,4-methylenedioxy)phenethyl]-5-[(3-carboxamido-4-hydroxy)-α-hydroxybenzyl]pyrrolidine were dissolved in distilled water. Isoproterenol and norepinephrine were dissolved in normal saline.

Experimental Protocol

Isoproterenol was administered i.v. at half-log interval doses from 0.0158 μg/kg to 0.5 μg/kg. Norepinephrine was administered at 0.316 μg/kg and 1 μg/kg 50 μl of investigational drug solution (i.e. either Timolol or ±2-[(3,4-methylenedioxy)phenethyl]-5-[(3-carboxamido-4-hydroxy)-α-hydroxybenzyl]pyrrolidone or 50 μl of H2O as a vehicle control, was delivered into the inferior conjunctual sac of an eye with a micropipette. Isoproterenol and norepinephrine dose-response curves were again run hourly for up to 6 hours. Intraocular pressure was measured immediately before administration of drugs or vehicle control, and again hourly just prior to the dose-response curves to isoproterenol and norepinephrine.

Results

Timolol administered to the eye at 0.5% produced significant decreases in intraocular pressure. Timolol was not eye irritating at 0.5%, but was eye irritating at 2%.

±2-[(3,4-methylenedioxy)phenethyl]-5-[(3-carboxamido-4-hydroxy)-α-hydroxybenzyl]pyrrolidine administered to the eye decreased IOP at 0.5, 1 and 2%, but to a lesser extent than Timolol. The results were, however, comparable to those seen in rabbits and described in Example 20.

Effect on Blood Pressure and Heart Rate

Ocular administration of Timolol produced marked decreases in baseline blood pressure and heart rate at all three doses (0.25%, 0.5%, 2%). Both parameters reached a nadir by 90 minutes post-dose.

Baseline blood pressure and heart rate in animals treated with 1% or 2% ±2-[(3,4-methylenedioxy)-phenethyl]-5-[(3-carboxamido-4-hydroxy)-α-hydroxybenzyl]pyrrolidine) differed little from control dogs.

Inhibition of Isoproterenol Responses

Ocular Timolol at 0.5%, 0.25%, and 2% markedly inhibited i.v. (systemic) isoproterenol challenges at 1, 2, and 3 hours after administration indicating that Timolol is readily absorbed systemically following ocular administration.

±2-[(3,4-methylenedioxy)-phenethyl]-5-[(3-carboxamido-4-hydroxy)-α-hydroxybenzyl]pyrrolidine produced some inhibition of isoproterenol and norepinephrine responses. However, the effects were not dose related either from the standpoint of the blocking drug or the challenge drugs.

Conclusion

The present studies demonstrate that the pentobarbital anesthetized dog represents an excellent model for screening of systemic effects of ocularly administered adrenergic blocking agents. The typical systemic side effects of timoptic observed in man were eluted following ocular administration.

At the doses tested, the ±2-[(3,4-methylenedioxy)-phenethyl]-5-[(3-carboxamido-4-hydroxy)-α-hydroxybenzyl]pyrrolidine lowered intraocular pressure, produced modest, if any systemic effect and no irritation to the eye.

What is claimed is:

1. A method for treating elevated intraocular pressure in a mammal, which method comprises administering directly to the eye of a mammal in need of such treatment a therapeutically effective amount of a compound chosen from those represented by the formula

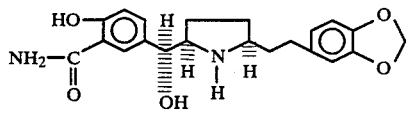

namely, ±2-[(3,4-methylenedioxy)phenethyl]-5-[(3-carboxamido-4-hydroxy)-α-hydroxybenzyl]pyrrolidine or a pharmaceutically acceptable acid addition salt thereof.

2. The method of claim 1 for treatment of glaucoma.

3. A method for treating elevated intraocular pressure in a mammal, which method comprises administering directly to the eye of a mammal in need of such treatment a therapeutically effective amount of a compound chosen from those represented by the formula

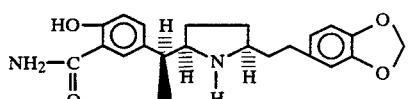

and its enantiomer, namely, (±), (+), and (−) cis erythro 2-[(3,4-methylenedioxy)phenethyl]-5-[(3-carboxamido-4-hydroxy)-α-hydroxybenzyl]pyrrolidine or a pharmaceutically acceptable acid addition salt thereof.

4. The method of claim 3 for treatment of glaucoma.

5. A method for treating elevated intraocular pressure in a mammal, which method comprises administering directly to the eye of a mammal in need of such treatment a therapeutically effective amount of a compound chosen from those represented by the formula

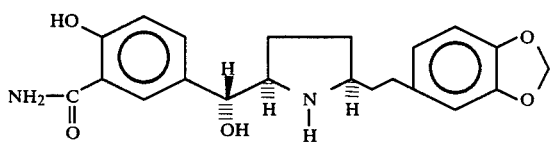

and its enantiomer, namely, (±), (+), and (−) cis threo 2-[(3,4-methylenedioxy)phenethyl]-5-[(3-carboxamido-4-hydroxy)-α-hydroxybenzyl]pyrrolidine or a pharmaceutically acceptable acid addition salt thereof.

6. The method of claim 5 for treatment of glaucoma.

7. A method for treating elevated intraocular pressure in a mammal, which method comprises administering directly to the eye of a mammal in need of such treatment a therapeutically effective amount of a compound chosen from those represented by the formula

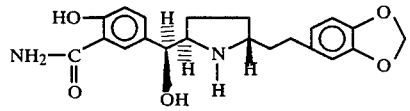

and its enantiomer, namely, (±), (+), and (−) trans erythro 2-[(3,4-methylenedioxy)phenethyl]-5-[(3-carboxamido-4-hydroxy)-α-hydroxybenzyl]pyrrolidine or a pharmaceutically acceptable acid addition salt thereof.

8. The method of claim 7 for treatment of glaucoma.

9. A method for treating elevated intraocular pressure in a mammal, which method comprises administering directly to the eye of a mammal in need of such treatment a therapeutically effective amount of a compound chosen from those represented by the formula

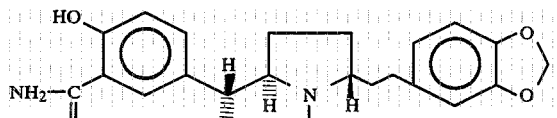

and its enantiomer, namely, (±), (+), and (−) trans 2-[(3,4-methylenedioxy)phenethyl]-5-[(3-carboxamido-4-hydroxy)-α-hydroxybenzyl]pyrrolidine or a pharmaceutically acceptable acid addition salt thereof.

10. A topical ophthalmologically acceptable pharmaceutical composition for treatment of elevated intraocular pressure in a mammal which composition comprises an ophthalmologically acceptable excipient in admixture with 0.001% to 10% wt/vol a compound of formula

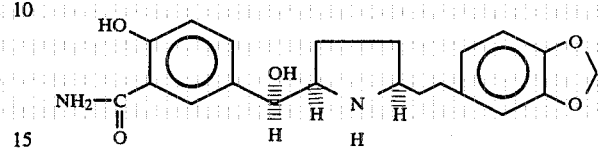

namely, ±2-[(3,4-methylenedioxy)phenethyl]-5-[(3-carboxamido-4-hydroxy)-α-hydroxybenzyl]pyrrolidine or a pharmaceutically acceptable acid addition salt thereof in admixture with a pharmaceutically acceptable excipient.

11. The composition of claim 10 wherein the composition is a sterilized aqueous solution which contains 0.005% to 1% wt/vol of the active ingredient.

* * * * *